(12) United States Patent
Niger et al.

(10) Patent No.: US 6,555,711 B1
(45) Date of Patent: Apr. 29, 2003

(54) α-AMINO-N-ALLYLAMIDINO NITROBENZENE COMPOUND AND SYNTHESIS

(75) Inventors: Robert J. Niger, Rochester, NY (US); William B. Vreeland, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/246,552

(22) Filed: Sep. 18, 2002

(51) Int. Cl.[7] .............................................. C07D 211/60
(52) U.S. Cl. .................... 564/246; 548/371.7; 548/561
(58) Field of Search ....................... 564/246; 548/371.7, 548/561

(56) References Cited

U.S. PATENT DOCUMENTS

| 4,705,863 A | 11/1987 | Sato et al. |
|---|---|---|
| 6,020,498 A | 2/2000 | Ferruccio et al. |

*Primary Examiner*—Samuel Barts
(74) *Attorney, Agent, or Firm*—Arthur E. Kluegel

(57) ABSTRACT

Disclosed is a process comprising reacting an N-allylimino nitrobenzene compound with a diaminodinucleophile to form an α-amino-N-allylamidino nitrobenzene compound and the compound itself.

20 Claims, No Drawings

α-AMINO-N-ALLYLAMIDINO NITROBENZENE COMPOUND AND SYNTHESIS

FIELD OF THE INVENTION

This invention relates to an α-amino-N-allylamidino nitrobenzene compound and process for its preparation.

BACKGROUND OF THE INVENTION

The photographic art employs couplers to provide colored dyes in image reproductions. The couplers react imagewise with color developer to produce the desire reproduction. One of the couplers useful for this purpose is a pyrazolo[1,5-b][1,2,4]triazole compound that has found utility for forming a magenta dye in the usual system employing subtractive primaries.

Such couplers and methods of making them were originally disclosed in U.S. Pat. No. 4,621,046. Other methods have been disclosed in U.S. Pat. Nos. 4,705,863 and 6,020,498. The latter patent suggests the use of certain N-alkylamidino nitrobenzene derivatives for synthesizing intermediates in the process. It is desirable, however to provide alternative processes for preparing the desired compounds, especially processes that can provide improved yields.

SUMMARY OF THE INVENTION

The invention provides a process comprising reacting an N-allylimino nitrobenzene compound with a diaminodinucleophile to form an α-amino-N-allylamidino nitrobenzene compound and also provides the compound itself as a composition of matter.

The invention provides a useful process for synthesizing useful compounds employing allyl groups. Embodiments of the invention can provide improved yields compared to prior art processes.

DETAILED DESCRIPTION OF THE INVENTION

The invention is summarized above. The process of the invention is generally shown in reaction scheme 3 in the following scheme.

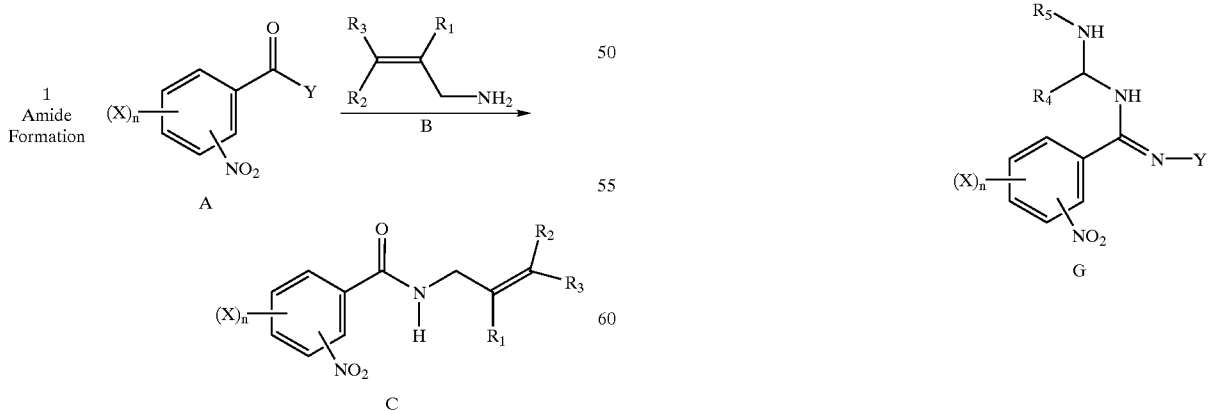

3
-continued
5 Oxime Transformation
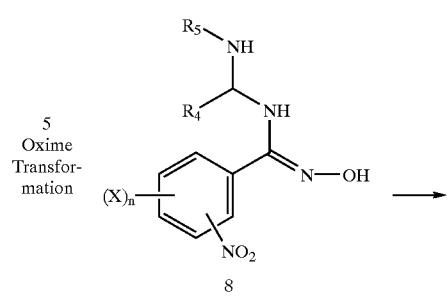
8
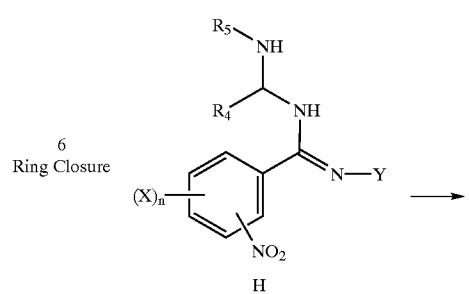
H
6 Ring Closure
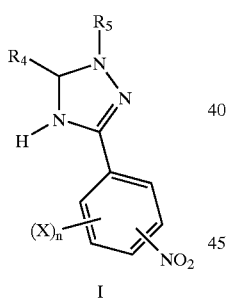
I
Reaction Scheme (specific)
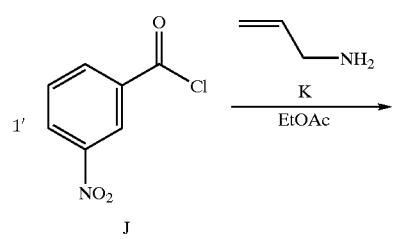
J
4
-continued
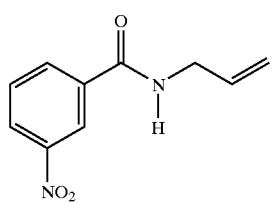
L
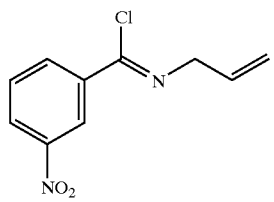
M
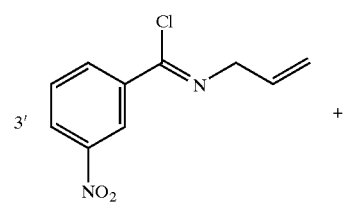
M
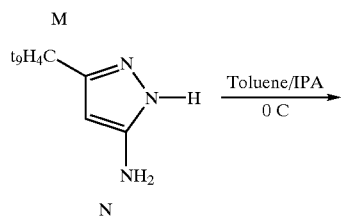
N
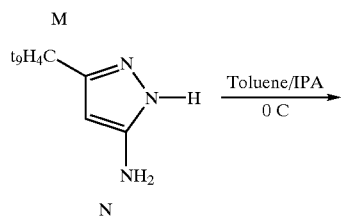
O -continued

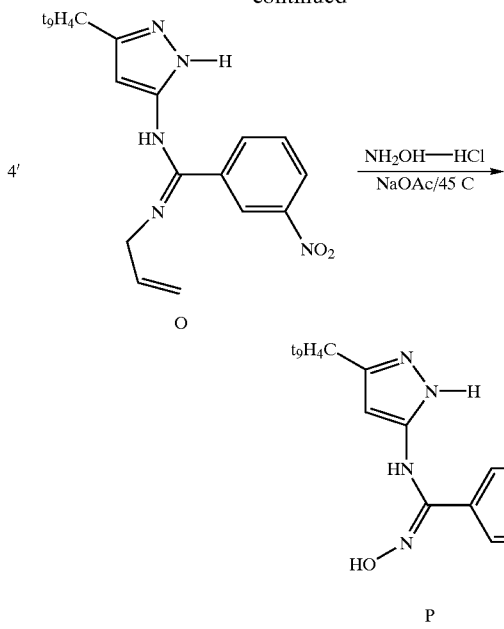

In reaction 3, an N-allylimino nitrobenzene compound is reacted with a diaminodinucleophile to form an α-amino-N-allylamidino nitrobenzene compound. Suitably, the reaction is carried out in the presence of a solvent that is inert under the reaction conditions. Useful solvents may be selected from the group consisting of $C_1$ to $C_8$ aliphatic alcohols, chlorinated or unchlorinated aromatic hydrocarbons such as toluene, the xylenes, monochlorobenzene or dichlorobenzenes, chlorinated or unchlorinated aliphatic hydrocarbons, ethers such as tetrahydrofuran, and esters such as ethyl acetate or isopropyl acetate. Preference is given to using alcohols, in particular isopropyl alcohol. In particular the reaction may be carried out using a mixture of toluene and isopropyl alcohol where the 3-tert-butyl-5-aminopyrazole in an isopropyl alcohol solution is added to a toluene solution of the amidine.

The reaction is exothermic and conveniently carried out at a temperature ranging from −10° C. to +30° C. and desirably from 0 to 15° C.

The reaction is carried out with the diaminodinucleophile being present in stoichiometric quantity or in excess compared to the α-amino-N-allylamidino nitrobenzene compound, with an excess of up to 0.5 mols/mol and a range of 1 to 1.25 mols/mol preferred. The compound is one having at least two nucleophilic nitrogen atoms and may include a ring compound such as an 3-tert-butyl-5-aminopyrazole.

Reaction 3 is typically described using the above captioned equation and the following limitations:

Z and X may independently be halogen, alkoxy, aryloxy, alkylthio, arylthio or heterocyclic groups;

$R_1$, $R_2$, and $R_3$ may independently be hydrogen, halogen, alkoxy, aryloxy, alkylthio, arylthio, (cyclo-)alkyl, alkenyl, alkynyl, silyl or heterocyclic groups; provided that $R_1$, $R_2$, and $R_3$ may also be contained within a carbocyclic or heterocyclic aromatic or non-aromatic ring system;

$R_4$ and $R_5$ may independently be hydrogen, halogen, alkoxy, aryloxy, alkylthio, arylthio, alkyl, alkenyl, alkynyl, silyl or heterocyclic groups; provided that $R_4$ and $R_5$ may also be contained within a carbocyclic or heterocyclic aromatic or non-aromatic ring system; and Y is a leaving group such as hydroxy, halogen, alkoxy, aryloxy, acetoxy, siloxy, mesylate or tosylate. The preferred leaving groups are mesylate or tosylate.

The reaction may be represented by the following reaction 3

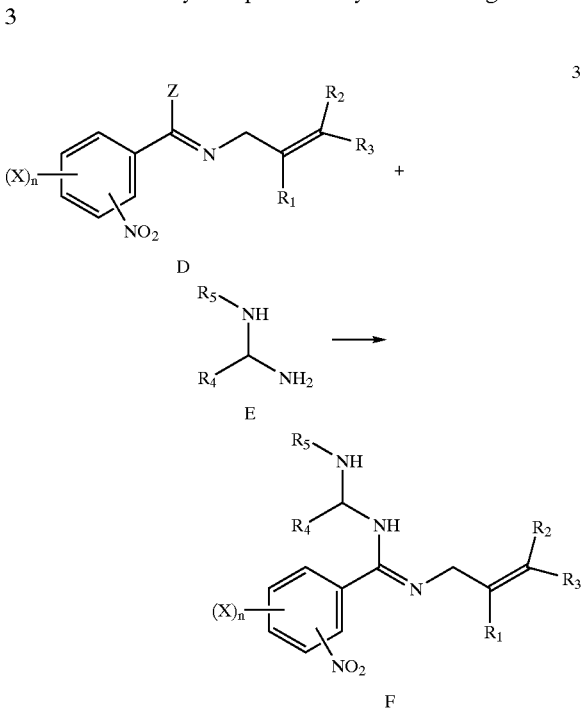

wherein
Z and X are independently selected from halogen, alkoxy, aryloxy, alklthio, arylthio and heterocyclic akyl groups and n is 0 to 4;

$R_1$, $R_2$, $R_3$ are independently selected from H, halogen, alkoxy, aryloxy, alkylthio, arylthio, alkyl, saturated or unsaturated cyclohydrocarbyl, heterocylic, aroyl, alkenyl, alkynyl, and silyl groups, provided that $R_1$, $R_2$, $R_3$ may also be contained within a ring system; and $R_4$ and $R_5$ are independently selected from H, halogen alkoxy, aryloxy, alkylthio, arylthio, alkyl, saturated or unsaturated cyclohydrocarbyl, hetereocylic, aromatic, aryl, alkenyl, alkynyl, silyl, provided that $R_4$ and $R_5$ may also be contained within a ring system.

The starting amide can be prepared using known methods, for example where the amine can be reacted with an acyl halide, an anhydride, an ester, or direct coupling with a carboxylic acid. (Woodcock, D. J. in Patai *The Chemistry of the Amino Group*; Wiley: N.Y., 1968, p. 440.)

In order to carry out step 2, use is generally made of a chlorinating agent such as, in particular, thionyl chloride ($SOCl_2$), phosphorus pentachloride ($PCl_5$), phosphorus oxychloride ($POCl_3$), phosgene ($COCl_2$), or oxalyl chloride ($COCl)_2$, or one of their mixtures as more fully described in:

$SOCl_2$ Lawson, A.; Miles, D. H.; J Chem Soc [JCSOA9] 1959, 2865.

$POCL_3$ Harris, R. L. N.; Synthesis [SYNTBF] 1980 (10), 841.

$PCl_5$ Madronero, R.; Vega, S.; Synthesis [SYNTBF] 1987 (7), 628.

$(COCl)_2$ Fujisawa, T.; Mori, T.; Sato, T.; Tetrahedron Lett [TELEAY] 1982, 23 (48), 5059.

Preference is given to using thionyl chloride. The chlorinating agent is employed in stoichiometric quantity or in excess. For reasons of economy, the quantity of chlorinating agent is preferably from 1 to 1.25 mol per mol of amide. The reaction can be carried out without solvent, with the chlorinating agent then serving as the solvent, or in the presence of a solvent or a mixture of solvents which are inert under the reaction conditions and which are selected from chlorinated or unchlorinated aromatic hydrocarbons such as toluene, the xylenes, monochlorobenzene or the dichlorobenzenes, or chlorinated or unchlorinated aliphatic hydrocarbons such as ethane or dichloromethane. Toluene is very suitable.

The temperature of this reaction is generally between 25° C. and the reflux temperature of the solvent. When toluene is the chosen solvent and the chlorinating agent is thionyl chloride, the temperature is, in particular, between 70° C. and 110° C.

Catalysts such as N,N-dialkylated amides, in particular dialkylated formamides whose alkyl groups possess from 1 to 8 carbon atoms, such as N,N-dimethylformamide and, more especially, N,N-dibutylformamimde, can be added in order to accelerate the reaction. In general, the chlorination lasts between 2 and 15 hours. Once the reaction has finished, it is not necessary to isolate the chloroimine that is formed from the reaction medium.

General conditions for forming the oxime are described in the following literature:

C. G. McCarty, "*Chemistry of the Carbon-Nitrogen Double Bond*" Ed. S. Patai, Interscience, New York (1970), pp 408–439;

J. A. Gautier, M. Miocque and C. C. Farnoux, "The Chemistry of Amidines and Imidates", Ed. S. Patai, Interscience, New York, (1975) pp 313–314.

Steps 5 and 6 are ring closure reactions and are more fully described in U.S. Pat. No. 4,705,863.

Unless otherwise specifically stated, use of the term "group", "substituted" or "substituent" means any group or radical other than hydrogen. Additionally, when reference is made in this application to a compound or group that contains a substitutable hydrogen, it is also intended to encompass not only the unsubstituted form, but also its form further substituted with any substituent group or groups as herein mentioned, so long as the substituent does not destroy properties necessary for the intended utility. Suitably, a substituent group may be halogen or may be bonded to the remainder of the molcule by an atom of carbon, silicon, oxygen, nitrogen, phosphorous, or sulfur. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, cyclohexyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, andp-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired desirable properties for a specific application and can include, for example, hydrophobic groups, solubilizing groups, blocking groups, and releasing or releasable groups. When a molecule may

EXAMPLES

Example 1

Step 1' A 2-L, three-necked, round-bottomed flask equipped with a magnetic stirring bar, a 24/40 adapter fitted with a thermometer, an argon inlet adapter, and a 250-mL pressure-equalizing addition funnel fitted with a glass stopper was purged with argon. The flask was charged with 3-nitrobenzoyl chloride (J) 112.0 g (0.6035 mol) and 850 mL of dichloromethane, and then cooled with an ice-water bath. The addition funnel was charged with triethylamine 93.0 mL (0.667 mol) and allylamine (K) 50.0 mL (0.666 mol), and this solution was then added dropwise to the reaction mixture over ca. 2.5 h while the reaction temperature was maintained at 0–4° C. The addition funnel was then rinsed with two 5-mL portions of dichloromethane. The resulting turbid pale orange-pink reaction mixture was allowed to slowly warm to and stir at room temperature. After 16.5 h, 600 mL of 1N HCL was added to the turbid bright yellow solution over 30 sec and the biphasic mixture was transferred to a separatory funnel. The reaction flask was rinsed with three 100-mL portions of 1:1 $CH_2Cl_2$: 1N HCl and the organic phase was separated and washed with 500 mL of saturated sodium chloride solution, dried over sodium sulfate, filtered, and concentrated under reduced pressure to afford 122 g (98% crude yield) of a pale yellow solid. The crude product was recrystallized from 450 mL of toluene to afford 113 g (91 % yield) of N-allyl-3-nitrobenzamide (L) as a powdery pale yellow solid.

$^1$H NMR spectrum ($CDCl_3$, 300 MHz), δ (ppm):4.11 (tt, J=6.0, 3.0 Hz, 2H), 5.21 (dq, J=10.5, 3.0 Hz, 1H), 5.28 (dq, J=16.5, 3.0 Hz, 1H), 5.87–6.00 (m, 1H), 6.62 (br s, 1H), 7.64 (appar. t, J=9.0 Hz, 1H), 8.18 (appar. dt, J=9.0, 1.5 Hz, 1H), 8.35 (ddd, J=6.0, 3.0, 1.5 Hz, 1H), 8.60 (appar. t, J=3.0 Hz, 1H). LRMS m/z 205 (M$^-$).

Step 2' A 50-mL, one-necked, round-bottomed flask equipped with a magnetic stirring bar and a reflux condenser fitted with an argon inlet adapter was evacuated and purged with argon three times and then maintained under an atmosphere of argon during the course of the reaction. The flask was charged with N-allyl-3-nitrobenzamide (L) 5.15 g (0.025 mol) and thionyl chloride 12.2 mL (0.167 mol), and then the clear pale yellow reaction mixture was heated to reflux over 50 min. After stirring at reflux for 2.25 h, the oil bath was removed and the clear yellow reaction mixture was allowed to cool to room temperature over 45 min. The magnetic stirring bar was removed and rinsed along with the condenser using a total of ca. 10 mL toluene. The yellow solution was concentrated at reduced pressure to afford the chloroimine M as a dark yellow liquid. The chloroimine M was treated with five successive 6-mL portions of toluene and each time the toluene was removed under reduced pressure. The product was used in the next step without purification.

Step 3' A 50-mL, one-necked, round-bottomed flask containing the chloroimine M equipped with a magnetic stirring bar and a 30-mL pressure-equalizing addition funnel fitted with an argon inlet adapter was purged with argon. The flask was charged with 6 mL of toluene and then cooled with an ice-water bath. Then a solution of 3-tert-butyl-5-aminopyrazole (N) 3.45 g (0.025 mol) in 9 mL of isopropyl alcohol was added dropwise via addition funnel over 1.25 h. The addition funnel was then rinsed with two 5-mL portions of isopropyl alcohol, the ice-water bath was removed and the clear orange-yellow reaction mixture was stirred at room temperature for 19 h and then the N-allylamidine O in toluene-isopropyl alcohol was used in the next step without purification. Preparation, isolation, and characterization of this intermediate, N-allylamidine O, can be found in Example 5.

Step 4' A 100-mL, three-necked, round-bottomed flask equipped with a magnetic stirring bar, a reflux condenser fitted with an argon inlet adapter, and two glass stoppers was evacuated and purged with argon three times and then maintained under an atmosphere of argon during the course of the reaction. The flask was charged with the solution of N-allylamidine O in toluene-isopropyl alcohol prepared in the previous reaction and a total of 10 mL of methanol was used to aid in the transfer. The flask was then charged with hydroxylamine hydrochloride 3.63 g (0.052 mol) and the slightly turbid pale orange reaction mixture was heated to 40° C. over 45 min followed by the addition of sodium acetate 1.95 g (0.024 mol) in one portion. The resulting yellow heterogeneous reaction mixture was stirred at 40–48° C. for 20.5 h. The reaction mixture was then partially concentrated under reduced pressure using an aspirator followed by the addition of 25 mL total of ca. 50° C. water to the viscous yellow slurry in portions over ca. 1 min. After stirring at 40–44° C. for ca. 1.5 h, the oil bath was removed and the biphasic yellow solution was allowed to cool to room temperature over 55 min. The biphasic yellow-green solution was diluted with 25 mL of ethyl acetate and transferred to a separatory funnel with the aid of three 10-mL portions of 1:1 EtOAc:$H_2O$. The green-yellow organic phase was separated and washed with 25 mL of water, 25 mL of saturated sodium chloride solution, dried over sodium sulfate, filtered and concentrated under reduced pressure. The resulting yellow-green glass was treated with five successive 50-mL portions of dichloromethane and each time the dichloromethane was removed under reduced pressure. Further concentration under high vacuum afforded 7.3 g (96% crude yield based upon the starting amide) of the amidoxime P as a yellow-green glass which was 86% pure by LC. By multiplying the crude yield times the LC purity a final yield of 83% was obtained. $^1$H NMR and mass spec were consistent with the product.

$^1$H NMR spectrum (DMSO, 300 MHz), δ (ppm): 1.12 (s, 9H), 5.45 (s, 1H), 7.56 (appar. t, J=7.5 Hz, 1H), 7.76 (appar. d, J=9.0 Hz, 1H), 8.06 (appar. t, J=3.0 Hz, 1H), 8.08 (s, 1H), 8.13 (appar. d, J=6.0 Hz, 1H), 10.60 (s, 1H), 11.70 (br s, 1H). LRMS m/z 302 (M$^-$).

Example 2

Step 1' A 3-L, three-necked, round-bottomed flask equipped with a mechanical stirrer, a nitrogen inlet adapter, and a 500-mL pressure-equalizing addition finnel fitted with a glass stopper was purged with nitrogen. The flask was charged with allylamine (K) 33.9 g (0.593 mol), 50 mL of ethyl acetate, triethylaamine 60.0 g (0.593 mol), and then cooled with an ice-water bath. The addition funnel was charged with 3-nitro-benzoyl chloride (J) 100.0 g (0.539 mol) and 230 mL ethyl acetate, and this solution was then added dropwise to the reaction mixture over 1 h while the reaction mixture was maintained at 0° C. The reaction mixture was stirred at 0° C. for 3 h and then filtered. The filtrate was transferred to a separatory finnel and washed with 150 mL of a 10% (by volume) HCl aqueous solution, 100 mL of saturated sodium chloride solution, dried over magnesium sulfate, and the solvent volume was reduced to one-third the original volume under reduced pressure. The clear solution was cooled to 0° C. overnight. The resulting yellow solid was collected by filtration and dried in a vacuum oven at 50° C. for 6 h to afford 89.4 g (80% yield) of N-allyl-3-nitrobenzamide (L) as a yellow solid.

Step 2' A 1 -L, one-necked, round-bottomed flask equipped with a magnetic stirring bar and a reflux condenser fitted with a nitrogen inlet adapter was purged with nitrogen. The flask was charged with N-allyl-3-nitrobenzamide (L) 85.0 g (0.412 mol), thionyl chloride 383.5 g (3.22 mol), three drops of DMF, and the reaction was stirred at reflux for 2.5 h. The excess thionyl chloride was then removed under reduced pressure. The resulting chloroimine M (yellow oil) was treated with three successive 75-mL portions of toluene and each time the toluene was removed under reduced pressure. The chloroimine M was dissolved in 50 mL of toluene and used in the next step without purification.

Step 3' A 3-L, three-necked, round-bottomed flask equipped with a mechanical stirrer, a nitrogen inlet adapter, and a 250-mL pressure-equalizing addition funnel fitted with a glass stopper was purged with nitrogen. The flask was charged with the solution of chloroimine M in 50 mL of toluene and the flask was placed in an ice-water bath. Separately, a 1 -L, one-necked, round-bottomed flask was charged with 3-tert-butyl-5-aminopyrazole (N) 61.94 g (0.445 mol) and 150 mL of toluene. The toluene was removed under reduced pressure. The resulting red oil was dissolved in 110 mL of isopropyl alcohol and transferred to the addition funnel. The solution of 3-tert-butyl-5-aminopyrazole (N) in 110 mL of isopropyl alcohol was added dropwise via addition funnel to the 0° C. solution of chloroimine M in toluene over 1.25 h while maintaining a reaction temperature of 0–10° C. The reaction mixture was stirred at 0° C. for 2 h and at the end of this time, an orange precipitate formed.

Step 4' A 3-L, three-necked, round-bottomed flask containing the solution of N-allylamidine O in toluene-isopropyl alcohol equipped with a mechanical stirrer, a glass stopper, and a reflux condenser fitted with a nitrogen inlet adapter was purged with nitrogen. The flask was charged with 280 mL of methanol, hydroxylamine hydrochloride 57.26 g (0.824 mol), and placed in an oil bath. The reaction mixture was heated and upon reaching 45° C., sodium acetate 40.56 g (0.494 mol) was added in one portion. The reaction was stirred at 45° C. for 14 h. The reaction mixture was then cooled to room temperature and 300 mL of a 10% HCL/$H_2O$ was solution was added. The biphasic solution was transferred to a separatory funnel and the organic layer was recovered. The aqueous layer was extracted with two 150-mL portions of ethyl acetate. The combined organic layers were dried over magnesium sulfate and concentrated under reduced pressure. The resulting dark yellow oil was treated with three successive 1 50-mL portions of dichloromethane and each time the solvent was removed under reduced pressure. Further concentration under high vacuum afforded 102 g (80% crude yield based upon the starting amide) of the amidoxime P as a yellow solid which was 89% pure by LC. By multiplying the crude yield times the LC purity a final yield of 73% was obtained. $^1$H NMR and mass spec was consistent with product data in Example 1.

Example 3

Comparative as Taught in U.S. Pat. No. 6,020,498

A 250-mL, one-necked, round-bottomed flask equipped with a magnetic stirring bar and a reflux condenser fitted with a nitrogen inlet adapter was purged with nitrogen. The flask was charged with N-propyl-3-nitrobenzamide 9.0 g (0.043 mol), thionyl chloride 40.0 g (0.336 mol), and several drops of DMF. The reaction mixture was stirred at reflux for 2 h. The excess thionyl chloride was then removed under reduced pressure. The resulting yellow oil was treated with two successive 10-mL portions of toluene and each time the toluene was removed under reduced pressure. The yellow oil was dissolved in 15 mL of toluene and used without purification. The reflux condenser was replaced with a 60-mL pressure-equalizing addition funnel and the flask was placed in an ice-water bath. The addition funnel was charged with 3-tert-butyl-5-aminopyrazole (N) 6.47 g (0.046 mol) dissolved in 35 mL of isopropyl alcohol and this solution was added dropwise via addition funnel to the 0° C. solution of chloroimine in toluene over 0.5 h. The reaction mixture was stirred at 0° C. for 5 h and then allowed to warm to 20 ° C. over 4 h. After stirring at 20° C. for an additional 3 days, approximately two-thirds of the solvent was removed under reduced pressure to afford an orange slurry.

A 250-mL, one-necked, round-bottomed flask containing the orange slurry equipped with a magnetic stirring bar and reflux condenser fitted with a nitrogen inlet adapter was purged with nitrogen. The flask was charged with 20 mL of methanol, hydroxylamnine hydrochloride 6.72 g (0.097 mol), and placed in an oil bath. The reaction mixture was heated and upon reaching 45 ° C, sodium acetate 5.75 g (0.070 mol) was added in one portion. The reaction was stirred at 45° C. for 4 days. The final TLC and LC indicated a complex mixture with three major products present. Compared to an authentic sample of the amidoxime P, LC analysis indicated a 38% yield of product P.

Example 4

The procedure as described in Example 3, where R=methyl, afforded the amidoxime P in 46% yield by LC.

TABLE I

| | % Yield | | |
| --- | --- | --- | --- |
| Example | U.S. Pat. No. 6,020,498 | Allyl Modification | R |
| 1 | | 83% | $C_3H_5$ |
| 2 | | 73% | $C_3H_5$ |
| 3 | 38% | | $C_3H_7$-n |
| 4 | 46% | | $CH_3$ |

The data in Table I shows that preparation of the oxime intermediate of Example 3 following the prior art procedure taught in U.S. Pat. No. 6,020,498, gave the desired product in only 38–46% yield. Several other products were also produced during this reaction indicating competing, undesired, side reactions. In contrast, preparation of the oxime in the manner described in Examples 1 and 2 where N-allyl (i.e., Allyl Modification) was substituted for alkyl, resulted in significant increases in yields (83% and 73% respectively). No major side reactions were observed. Preparation of the 4-nitrobenzene oxime proceeded with similar yields that were comparable to the prior art.

Example 5

Synthesis of Isolated Intermediate N-allyl, N'-(3-tert-butyl-5-pyrazolyl)-4-nitrobenzamidine (O)

A 100-mL, one-necked, round-bottomed flask equipped with a magnetic stirring bar and a reflux condenser fitted with an argon inlet adapter was evacuated and purged with argon three times and then maintained under an atmosphere of argon during the course of the reaction. The flask was charged with N-allyl-3-nitrobenzamide (L) 5.15 g (0.025 mol), prepared as described previously in example 1, and thionyl chloride 12.2 mL (0.167 mol), and then the clear pale yellow reaction mixture was heated to reflux over 50 min. After 2 h, the oil bath was removed and the clear yellow reaction mixture was allowed to cool to room temperature over 25 min. The condenser was rinsed with three 1.5-mL portions of toluene and the yellow solution, containing the magnetic stirring bar, was concentrated under reduced pressure to afford the chloroimine M as a dark yellow liquid. The chloroimine M was treated with five successive 6-mL portions of toluene and each time the toluene was removed under reduced pressure. The product was used in the next step without purification.

A 100-mL, one-necked, round-bottomed flask containing the chloroimine M equipped with a magnetic stirring bar and a 30-mL pressure-equalizing addition funnel fitted with an argon inlet adapter was purged with argon. The flask was charged with 6 mL of toluene and then cooled with an ice-water bath. Then a solution of 3-tert-butyl-5-aminopyrazole (N) 3.45 g (0.025 mol) in 9 mL of isopropyl alcohol was added dropwise via addition fimnel over 1 h. The addition funnel was then rinsed with two 5-mL portions of isopropyl alcohol, the ice-water bath was removed and the clear orange-yellow reaction mixture was stirred at room temperature for ca. 5 days. The clear orange-yellow reaction mixture was then transferred to a separatory containing 100 mL of ethyl acetate and 100 mL of half-saturated sodium bicarbonate solution. The flask was rinsed with three 10-mL portions of 1:1 toluene:isopropyl alcohol. The yellow organic phase was separated and washed with 100 mL of water, 100 mL of saturated sodium chloride solution, dried over sodium sulfate, filtered and concentrated under reduced pressure. The resulting orange oil was treated with three successive 100-mL portions of dichloromethane and each time the dichloromethane was removed under reduced pressure. Further concentration under high vacuum afforded 8.0 g (98% crude yield based upon the starting amide) of the N-allylamidine O as a bright yellow solid which was 88% pure by LC. By multiplying the crude yield times the LC purity a final yield of 86% was obtained. The $^1$H NMR and mass spec were consistent with N-allyl, N'-(3-tert-butyl-5-pyrazolyl)-4-nitrobenzamidine (O).

$^1$H NMR spectrum (CDCl$_3$, 300 MHz), δ (ppm): 1.32 (s, 9H), 3.81 (br s, 2H), 5.15–5.31 (m, 2H), 5.77–5.90 (m, 1H), 6.02 (s, 1H), 7.57 (appar. t, J=7.5 Hz, 1H), 7.89 (appar. d, J=9.0 Hz, 1H), 8.26 (dd, J=9.0, 1.5 Hz, 1H), 8.43 (appar.t, J=3.0 Hz, 1H), 9.37 (br s, 1H). LRMS m/z 326 (M$^-$).

The entire contents of the patents and other publications referred to in this specification are incorporated herein by reference.

What is claimed is:

1. A process comprising reacting an N-allylimino nitrobenzene compound with a diaminodinucleophile to form an α-amino-N-allylamidino nitrobenzene compound.
2. The process of claim 1 wherein the reaction is carried out in the presence of a solvent that is inert under the reaction conditions.
3. The process of claim 2 herein the solvent is selected from the group consisting of $C_1$ to $C_8$ aliphatic alcohols, aromatic hydrocarbons, aliphatic hydrocarbons, ethers, and esters.
4. The process of claim 3 wherein the solvent comprises an aliphatic alcohol.
5. The process of claim 4 wherein the aliphatic alcohol is isopropyl alcohol.
6. The process of claim 1 wherein the reaction is carried out at a temperature ranging from −10° C. to +30° C.
7. The process of claim 1 wherein the reaction is carried out with the diaminodinucleophile being present the stoichiometric quantity or an excess compared to the N-allylimino nitrobenzene.
8. The process of claim 1 wherein the reaction is represented by equation 3

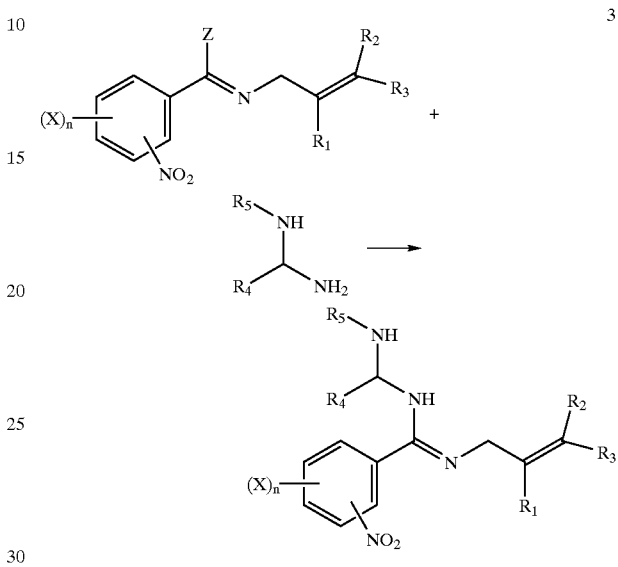

wherein
Z and X are independently selected from halogen, alkoxy, aryloxy, alkylthio, arylthio and heterocyclic alkyl groups and n is 0 to 4;
$R_1$, $R_2$, $R_3$ are independently selected from H, halogen, alkoxy, aryloxy, alkylthio, arylthio, alkyl, saturated or unsaturated cyclohydrocarbyl, heterocylic, aryl, alkenyl, alkynyl, and silyl groups, provided that $R_1$, $R_2$, $R_3$ may also be contained within a ring system; and
$R_4$ and $R_5$ are independently selected from H, halogen alkoxy, aryloxy, alkylthio, arylthio, alkyl, saturated or unsaturated cyclohydrocarbyl, heterocylic, aromatic, aryl, alkenyl, alkynyl, silyl, provided that $R_4$ and $R_5$ may also be contained within a ring system.

9. The process of claim 8 wherein $R_4$ and $R_5$ are joined to form a pyrazole ring system.
10. The process of claim 8 wherein $R_1$, $R_2$, and $R_3$ are H.
11. The process of claim 8 wherein Z is Cl.
12. The process of claim 8 wherein the nitro group is located para to the link to the allyl group.
13. The process of claim 8 wherein the nitro group is located meta to the link to the allyl group.
14. The process of claim 1 further including the preceding step of preparing the N-allylimino nitrobenzene compound by reacting the corresponding allylamidonitrobenzene compound with a chlorinating agent.
15. The process of claim 14 further including the still further preceding step of preparing the corresponding allylamidonitrobenzene compound by reacting the corresponding nitrobenzoyl compound bearing a leaving group with an allyl amine.
16. The process of claim 1 comprising the subsequent steps of forming the oxime and then closing the α-aminoamidino ring.
17. An α-amino-N-allylamidino nitrobenzene compound.
18. An α-amino-N-allylamidino-m-nitrobenzene compound.

19. An α-amino-N-allylamidino-p-nitrobenzene compound.

20. A nitrobenzene compound having the formula:

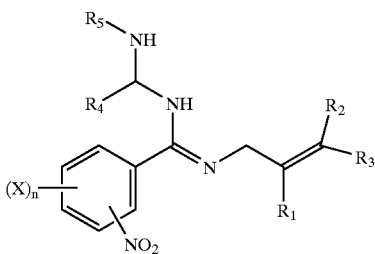

wherein x is independently selected from halogen, alkoxy, aryloxy, alkylthio, arylthio and heterocyclic alkyl groups and n is 0 to 4;

$R_1$, $R_2$, $R_3$ are independently selected from H, halogen, alkoxy, aryloxy, alkylthio, arylthio, alkyl, saturated or unsaturated cyclohydrocarbyl, heterocylic, aryl, alkenyl, alkynyl, and silyl groups, provided that $R_1$, $R_2$, $R_3$ may also be contained within a ring system; and $R_4$ and $R_5$ are independently selected from H, halogen alkoxy, aryloxy, alkylthio, arylthio, alkyl, saturated or unsaturated cyclohydrocarbyl, hetereocylic, aromatic, aryl, alkenyl, alkynyl, silyl, provided that $R_4$ and $R_5$ may also be contained within a ring system.

* * * * *